United States Patent
Li et al.

(10) Patent No.: US 11,515,025 B2
(45) Date of Patent: Nov. 29, 2022

(54) DOSIMETRY ASSESSMENT METHOD AND SYSTEM FOR ORGAN AT RISK IN ESOPHAGEAL RADIOTHERAPY PLAN

(71) Applicants: The Affiliated Hospital of Qingdao University, Qingdao (CN); Anhui University, Hefei (CN)

(72) Inventors: Teng Li, Hefei (CN); Huanting Li, Qingdao (CN); Xiaokun Hu, Qingdao (CN); Yan Wang, Hefei (CN); Dashan Jiang, Hefei (CN); Congxiao Wang, Qingdao (CN); Shifeng Liu, Qingdao (CN)

(73) Assignees: THE AFFILIATED HOSPITAL OF QINGDAO UNIVERSITY, Qingdao (CN); ANHUI UNIVERSITY, Hefei (CN)

( * ) Notice: Subject to any disclaimer, the term of this patent is extended or adjusted under 35 U.S.C. 154(b) by 0 days.

(21) Appl. No.: 17/437,845

(22) PCT Filed: Mar. 4, 2020

(86) PCT No.: PCT/CN2020/077844
§ 371 (c)(1),
(2) Date: Sep. 10, 2021

(87) PCT Pub. No.: WO2020/199836
PCT Pub. Date: Oct. 8, 2020

(65) Prior Publication Data
US 2022/0101974 A1 Mar. 31, 2022

(30) Foreign Application Priority Data
Apr. 1, 2019 (CN) .......................... 201910256615.3

(51) Int. Cl.
*G16H 20/40* (2018.01)
*G16H 20/10* (2018.01)
(Continued)

(52) U.S. Cl.
CPC ........... *G16H 20/10* (2018.01); *G06N 3/0445* (2013.01); *G06T 7/0012* (2013.01); *G16H 20/40* (2018.01);
(Continued)

(58) Field of Classification Search
CPC ...................................... G16H 20/40
See application file for complete search history.

(56) References Cited

U.S. PATENT DOCUMENTS

| | | | |
|---|---|---|---|
| 2019/0030370 A1* | 1/2019 | Hibbard | A61N 5/1045 |
| 2019/0051398 A1 | 2/2019 | Zankowski et al. | |
| 2020/0075148 A1* | 3/2020 | Nguyen | G16H 50/30 |

FOREIGN PATENT DOCUMENTS

| | | |
|---|---|---|
| CN | 104751498 A | 7/2015 |
| CN | 105358219 A | 2/2016 |

(Continued)

OTHER PUBLICATIONS

"Deep learning vs. machine learning: What's the difference"; Grieve; Jan. 23, 2020 (Year: 2020).*
(Continued)

*Primary Examiner* — John A Pauls
(74) *Attorney, Agent, or Firm* — Bayramoglu Law Offices LLC

(57) ABSTRACT

A dosimetry assessment method for an organ at risk (OAR) in an esophageal radiotherapy plan includes: acquiring volumetric-modulated arc therapy (VMAT) plan data of a patient with esophageal cancer, and obtaining a distance-target histogram (DTH); subjecting a geometric feature vector of the DTH to dimension reduction to obtain a dimension-
(Continued)

reduced geometric feature vector; establishing a deep belief network (DBN) model, and completing training the DBN model; non-linearly fitting a correlation between a dose feature vector and the dimension-reduced geometric feature vector to obtain a dose feature vector with a dimension being identical to a dimension of the dimension-reduced geometric feature vector; and reconstructing the dose feature vector through a decoding layer of an autoencoder structure to obtain a dose feature vector with a dimension being identical to a dimension of the geometric feature vector before the dimension reduction, and finally obtaining a dose-volume histogram (DVH) for predicting the OAR.

10 Claims, 5 Drawing Sheets

(51) Int. Cl.
  *G16H 50/30* (2018.01)
  *G06N 3/04* (2006.01)
  *G06T 7/00* (2017.01)

(52) U.S. Cl.
  CPC ... *G16H 50/30* (2018.01); *G06T 2207/10081* (2013.01)

(56) References Cited

FOREIGN PATENT DOCUMENTS

| | | |
|---|---|---|
| CN | 107441637 A | 12/2017 |
| CN | 109166613 A | 1/2019 |
| CN | 109859817 A | 6/2019 |
| WO | WO-2014068435 A2 * | 5/2014 ........... A61N 5/1031 |

OTHER PUBLICATIONS

Boltzmann Machines; Hinton; Mar. 25, 2007. (Year: 2007).*
"Stacks of Convolutional Restricted Boltzmann Machines for Shift-Invariant Feature Learning"; Norouzi et al.; IEEE; 2009 (Year: 2009).*
"A feasibility study for predicting optimal radiation therapy dose distributions of prostate cancer patients from patient anatomy using deep learning"; Dan Nguyen; 2017 (Year: 2017).*

* cited by examiner

DOSIMETRY ASSESSMENT METHOD AND SYSTEM FOR ORGAN AT RISK IN ESOPHAGEAL RADIOTHERAPY PLAN

CROSS REFERENCE TO THE RELATED APPLICATIONS

This application is the national phase entry of International Application No. PCT/CN2020/077844, filed on Mar. 4, 2020, which is based upon and claims priority to Chinese Patent Application No. 201910256615.3, filed on Apr. 1, 2019, the entire contents of which are incorporated herein by reference.

TECHNICAL FIELD

The present invention relates to the technical field of esophageal radiotherapy planning, and more particularly, to a dosimetry assessment method and system for an organ at risk (OAR) in an esophageal radiotherapy plan.

BACKGROUND

Esophageal radiotherapy planning is a time-consuming process that requires tedious parameter tuning to achieve the delivery of the maximum radiation dose under the planning target volume (PTV) while minimizing the radiation damage to the OAR. An important indicator to guide the tuning is the dose-volume histogram (DVH), which is used to measure the volume percentage of the organs receiving different radiation doses.

DVH is highly correlated with the geometric relationship between the PTV and the OAR. Modeling this correlation can significantly reduce the tuning time, and quickly realize a clinically accepted treatment plan by providing near-optimal plan parameters. Previous related studies have simulated the correlation between the DVH and the geometric relationship. By fitting the evolution of the skew normal parameters, the researchers proposed a three-parameter probability function of a distance to describe a function of a distance between the PTV as well as the OAR and a polynomial, and simulated their correlation with the DVH. In addition, some researchers calculated the volume fraction of the OAR corresponding to the PTV of different distances. They used the distance-target histogram (DTH) to represent the geometric relationship between the PTV and the OAR, and performed modeling through the correlation between the DTH and the DVH by component analysis and support vector regression (SVR).

The prior research, however, mainly focuses on the linear model of the extracted geometric features and the traditional machine learning (ML) method to simulate the correlation. These methods all have shortcomings such as low model robustness, low prediction accuracy and poor applicability. These problems increase the workload of the radiotherapist. In addition, the quality review standards for radiotherapy programs vary according to the difference between relevant clinical population statistical standards, which results in low accuracy of the calculated DVH.

SUMMARY

In order to overcome the shortcomings of the prior art, an objective of the present invention is to provide a dosimetry assessment method for an organ at risk (OAR) in an esophageal radiotherapy plan based on a deep belief network (DBN). The present invention adopts a deep learning (DL) method, and targets the specificity of the clinical individual, which reduces the burden of the radiotherapist, shortens the time for formulating the radiotherapy plan, and effectively improves the accuracy of the radiotherapy plan.

In order to solve the above technical problem, the present invention adopts the following technical means. A dosimetry assessment method for an OAR in an esophageal radiotherapy plan includes the following steps:

step 1: acquiring volumetric-modulated arc therapy (VMAT) plan data of a patient with esophageal cancer, including a computed tomography (CT) image and a structural contour image that are extracted;

step 2: calculating the VMAT plan data for the esophageal cancer to obtain a distance-target histogram (DTH);

step 3: subjecting a geometric feature vector of the DTH in step 2 to dimension reduction through an encoding layer in an autoencoder structure to obtain a dimension-reduced geometric feature vector;

step 4: establishing a deep belief network (DBN) model, iterating until convergence, and completing training the DBN model;

step 5: non-linearly fitting a correlation between a dose feature vector and the dimension-reduced geometric feature vector by the dimension-reduced geometric feature vector through a trained DBN to obtain a dose feature vector with a dimension being identical to a dimension of the dimension-reduced geometric feature vector;

step 6: reconstructing the dose feature vector of step 5 through a decoding layer of the autoencoder structure to obtain a dose feature vector with a dimension being identical to a dimension of the geometric feature vector before the dimension reduction, and finally obtaining a dose-volume histogram (DVH) for predicting the OAR.

Preferably, in step 2, the DTH is established by calculating a volume percentage of the OAR:

$$r(v^i_{OAR}, PTV) = \min_k \{\|v^i_{OAR} - v^k_{PTV}\| \mid v^k_{PTV} \in S_{PTV}\}$$

where, $v^i_{OAR}$ is an $i^{th}$ voxel of the OAR; $v^k_{PTV}$ is a $k^{th}$ voxel of a planning target volume (PTV); $S_{PTV}$ is a voxel set of the PTV; $r(v^i_{OAR}, PTV)$ is a Euclidean distance from the voxel of the OAR to a surface of the PTV Preferably, n coordinate points $((x_i, y_i), i \in 1, 2, \ldots, n)$ are selected from a curve of the DTH equidistantly along an x-axis; the selected n discrete coordinate points are used to represent the curve; each coordinate point includes a volume fraction value $y_i$ ($i \in 1, 2, \ldots, n$) and a corresponding distance value $x_i$ ($i \in 1, 2, \ldots, n$); $y_i$ denotes the volume fraction value of an $i^{th}$ coordinate; $y_i$ ($i \in 1, 2, \ldots, n$) is a vector element used to construct a geometric feature vector of an n-dimensional DTH; $x_i$ denotes the distance value of the $i^{th}$ coordinate.

Preferably, an encoder is composed of a plurality of encoding layers and a plurality of decoding layers;

each encoding layer reduces a dimension of an input through a compression of a fully connected layer, and an activation function of each neuron in the encoding layer is:

$$P(h_i = 1 \mid v_i) = \text{sigmoid}(c_i + W_i v_i)$$

where, $v_i$ is a feature vector as an input of an $i^{th}$ encoding layer after $(i-1)^{th}$ dimension reduction; $h_i$ is a feature vector as an output of the $i^{th}$ encoding layer after $i^{th}$ dimension reduction; $h_i$, $v_i \in \{0,1\}$; $W_i$ is a weight matrix of the $i^{th}$ encoding layer; $c_i$ is a deviation value of the $i^{th}$ encoding layer, where a dimension of $h_i$ is less than a dimension of $v_i$;

a process of the decoding layer is opposite to a process of the encoding layer; the decoding layer reconstructs an originally input feature vector by increasing a dimension of the input feature vector;

$$P(v_j = 1 | h_j) = \text{sigmoid}(b_j + W_j h_j)$$

where, $h_j$ is a feature vector as an input of a $j^{th}$ decoding layer after $(j-1)^{th}$ dimension increase; $v_1$ is a feature vector as an output of the $j^{th}$ decoding layer after $j^{th}$ dimension increase; $h_j$, $v_j \in \{0,1\}$; $W_j$ is a weight matrix of the $j^{th}$ decoding layer; $b_j$ is a deviation value of the $j^{th}$ decoding layer, where a dimension of $v_j$ is greater than a dimension of $h_j$.

Preferably, in step 4, the DBN model is formed by stacking a plurality of Boltzmann machines; a training process includes pre-training each of the Boltzmann machines and then stacking pre-trained Boltzmann machines to be a whole of a DBN for network fine-tuning training.

Preferably, the VMAT plan data of the patient with the esophageal cancer for training are first acquired as training set data, the CT image for training and the structural contour image for training are extracted from the training set data, and the DVH for training and the DTH for training are calculated; the dose feature vector of the DVH for training and the geometric feature vector of the DTH for training are calculated; a dimension-reduced dose feature vector of the DVH for training and a dimension-reduced geometric feature vector of the DTH for training are obtained through the decoding layer of the autoencoder structure;

each Boltzmann machine structure is pre-trained, where the each Boltzmann machine structure includes a corresponding visible layer v and hidden layer h;

iterating steps of the Boltzmann machine in the training process include: mapping the dimension-reduced geometric feature vector of the DTH in the visible layer to the hidden layer, reconstructing a new geometric feature vector of the DTH through a vector in the hidden layer, and mapping a reconstructed geometric feature vector of the DTH to the hidden layer, where, this process is expressed as a cycle, and each Boltzmann machine repeats three cycles in a pre-training process to update weight matrices in the visible layer and the hidden layer of the Boltzmann machine;

where, an objective loss function in each layer of the DBN is:

$$L(W, dt) = \alpha_s \|g - Y(dt)\|_2^2 + \|dt - Y'(g)\|_2^2 + \alpha_r \|W\|_1$$

where, dt is the dimension-reduced geometric feature vector of the DTH for training, and is further used as an input vector of the visible layer of each Boltzmann machine structure; $\alpha_s \|g-Y(dt)\|_2^2$ is a mean square error from the dimension-reduced geometric feature vector dt of the DTH for training to a feature vector g of the hidden layer; as is a constraint coefficient determined empirically in an experiment; a function Y represents a process from the visible layer to the hidden layer in the Boltzmann machine structure, and has an energy function as follows:

$$E(v, h | \theta) = -\sum_{i=1}^{n} a_i v_i - \sum_{j=1}^{m} b_j h_j - \sum_{i=1}^{n} \sum_{j=1}^{m} v_i W_{ij} h_j;$$

where, $\theta = \{W_{ij}, a_i, b_j\}$ is a parameter of the Boltzmann machine, which is a real number; $W_{ij}$ is a weight between a visible vector and a hidden vector; the visible layer has a total of i visible vector units (the visible vector refers to the vector dt of the dimension-reduced feature of the DTH for training); the hidden layer has a total of j hidden vector units; $a_i$ is an offset of an $i^{th}$ visible vector unit; $b_j$ is an offset of a $j^{th}$ hidden vector unit; $\|dt-Y'(g)\|_2^2$ is a mean square error between an input provided by the hidden vector g and a new geometric feature vector of the DTH obtained through reconstruction; Y' is an opposite process of Y, and represents the reconstruction of the new geometric feature vector of the DTH by the vector in the hidden layer; $\alpha_r \|W\|_1$ means an ensurement of a sparse expression in an equation by using a non-zero penalty factor; $\|W\|_1$ is L1 regularization of a weight matrix of each layer of the DBN; $\alpha_r$ is a sparse coefficient;

the training process of each Boltzmann machine is subjected to iterative cycles; when the objective loss function is less than 0.05, the objective loss function achieves a stable convergence to complete the training process, a parameter value of the Boltzmann machine is simultaneously stored to obtain a pre-trained Boltzmann machine model, and a plurality of pre-trained Boltzmann machine models are stacked into a pre-trained DBN.

Preferably, the dimension-reduced geometric feature vector of the DTH for training is re-input into the pre-trained DBN model for the fine-tuning training, and the loss function is a mean square error loss function:

$$L(W) = \frac{1}{2} \|dv\_i - D(dt)\|_2^2$$

when a loss value of the mean square error loss function is less than the set threshold, the mean square error loss function achieves a stable convergence, and the parameter value is stored to complete training the DBN model;

where, a function D denotes a pre-trained DBN model formed by stacking three Boltzmann machine structures; dt is the dimension-reduced geometric feature vector of the DTH for training; dv_i is an $i^{th}$ component of the dimension-reduced dose feature vector of the DVH for training obtained in step 3; i components require i different DBNs, and predicted outputs of the i DBNs correspond to a set of dimension-reduced dose feature vectors.

Preferably, in step 6, an n-dimensional dose feature vector is reconstructed through the decoding layer, and the reconstructed n-dimensional dose feature vector is used as an ordinate of a coordinate point of a new DVH, that is, $m'_j$ ($j \in 1, 2, \ldots, n$); a dose fraction value $n_j$ ($j \in 1, 2, \ldots, n$) is used as an abscissa of the coordinate point; where, new n coordinate points $((n_j, m'_j), j \in 1, 2, \ldots, n)$ are obtained; a curve drawn by connecting the n coordinate points is the DVH for predicting the OAR.

The present invention further provides a dosimetry assessment system for an OAR in an esophageal radiotherapy plan, including:

an encoding layer, configured to subject a geometric feature vector of a DTH to dimension reduction to obtain a dimension-reduced geometric feature vector;

a deep belief network (DBN) model, where a correlation between a dose feature vector and the dimension-reduced geometric feature vector is non-linearly fitted by the dimension-reduced geometric feature vector through a trained DBN to obtain a dose feature vector with a dimension being identical to a dimension of the dimension-reduced geometric feature vector;

a decoding layer, configured to reconstruct the dose feature vector to obtain a dose feature vector with a dimension being identical to a dimension of the geometric feature vector before the dimension reduction.

Preferably, the DBN model is formed by stacking a plurality of Boltzmann machines; a training process includes pre-training each of the Boltzmann machines and then stacking pre-trained Boltzmann machines to be a whole of a DBN for network fine-tuning training.

The present invention sampled the dose values of 50 coordinate points of the DVH at the beginning of a corresponding experiment, and then obtained 50 coordinate points, each coordinate point corresponding to the volume fraction value under the corresponding dose value.

The present invention has the following advantages. When the DVH of the OAR of a new patient is predicted, the DTH of the OAR is calculated first, then a 50-dimensional DTH feature vector is established by sampling the DTH curve, and the feature vector is simplified into a three-dimensional (3D) feature vector by an autoencoder. The corresponding 3D DVH feature vector can be obtained by mapping the corresponding DBN model. Finally, the DVH feature vector is reconstructed through the decoding layer in the autoencoder, thereby obtaining the predicted DVH of the OAR.

The present invention is an effective application of the DL technology. Compared with the prediction of the dosimetry features of esophageal cancer radiotherapy by the linear model extracting geometric features and the traditional machine learning (ML) method, the present invention performs automatic assessment of the dose of the OAR for the esophageal radiotherapy plan based on the geometric relationship between the OAR and the PTV. Experiments have shown that the model method can achieve accurate prediction of the DVH and can provide near-optimal parameters for the esophageal treatment plan, which can significantly shorten the time for formulating the esophageal radiotherapy plan and reduce the burden of the radiotherapist.

DETAILED DESCRIPTION OF THE EMBODIMENTS

Figure 1:
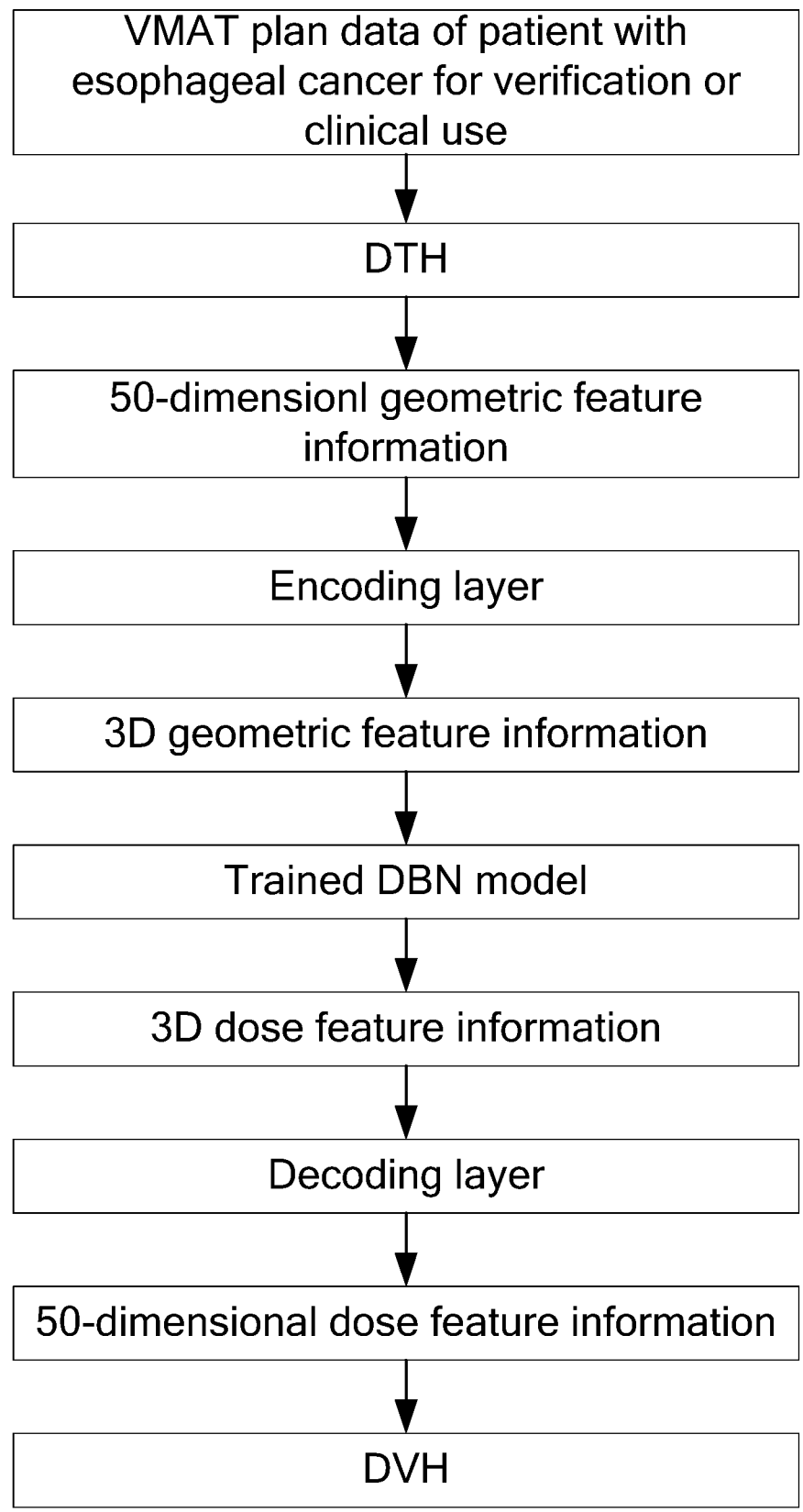
FIG. 1 is a flowchart according to Embodiment 1 of the present invention.
Figure 2:
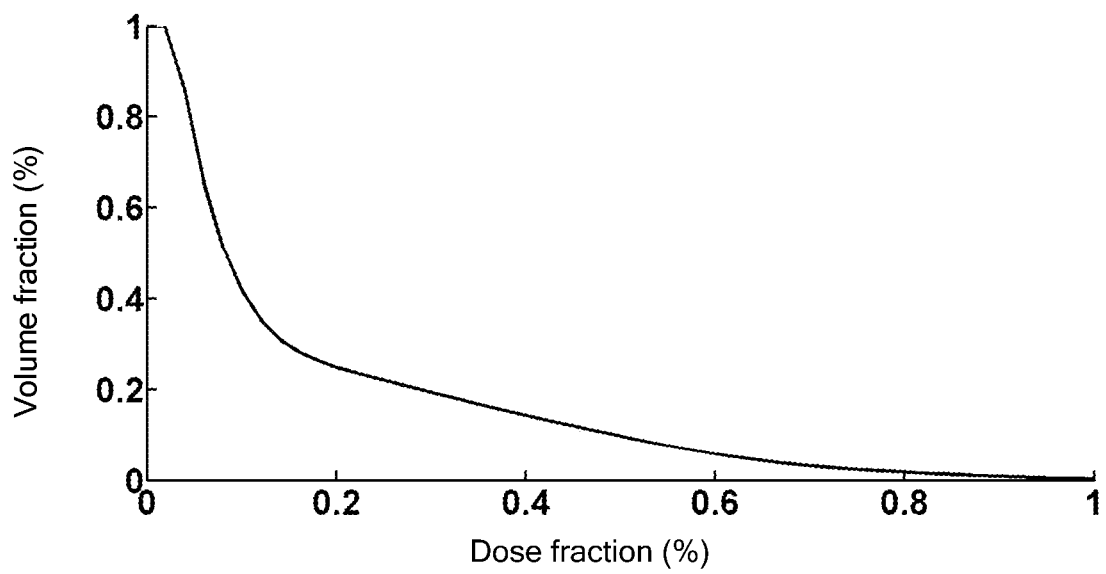
FIG. 2 is a dose-volume histogram (DVH) according to Embodiment 1 of the present invention.
Figure 3:
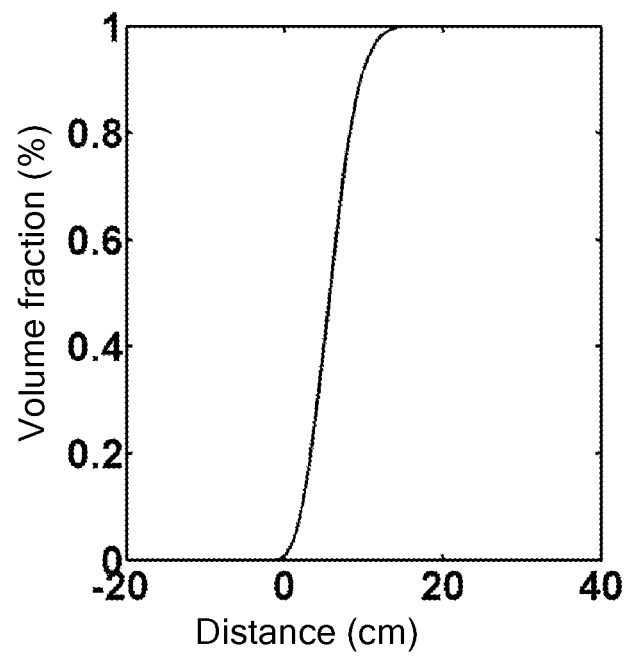
FIG. 3 is a distance-target histogram (DTH) according to Embodiment 1 of the present invention.

In order to make the objectives, technical solutions and advantages of embodiments of the disclosure clearer, the following text clearly and completely describes the technical solutions in the embodiments of the disclosure with reference to the embodiments of the disclosure. Apparently, the described embodiments are some rather than all of the embodiments. All other embodiments obtained by a person of ordinary skill in the art based on the embodiments of the disclosure without creative efforts shall fall within the protection scope of the disclosure.

An embodiment of the present invention provides a dosimetry assessment method for an organ at risk (OAR) in an esophageal radiotherapy plan. The method includes:

Step 1: Acquire volumetric-modulated arc therapy (VMAT) plan data of a patient with esophageal cancer. In this embodiment, a computed tomography (CT) image and a structural contour image are extracted from raw radiotherapy data through a Matlab-based computational environment for radiotherapy research (CERR) package.

Step 2: Calculate the VMAT plan data for esophageal cancer to obtain a distance-target histogram (DTH), and construct a geometric feature vector of the DTH.

The CT image is a cross-sectional or slice image. Each cross-sectional image has a thickness of 3 mm, representing a z-axis height, and it displays geometric information. According to the geometric structure information of an OAR and a planning target volume (PTV) represented in the structural contour image and the CT image, the spatial geometric distance between the OAR and the PTV and the overlap volume corresponding to the distance are calculated to draw the DTH.

The DTH is established by calculating a volume percentage of the OAR:

$$r(v^i_{OAR}, PTV) = \min_k \{\|v^i_{OAR} - v^k_{PTV}\| \mid v^k_{PTV} \in S_{PTV}\}$$

where, $v^i_{OAR}$ is an $i^{th}$ voxel of the OAR; $v^k_{PTV}$ is a $k^{th}$ voxel of a planning target volume (PTV); $S_{PTV}$ is a voxel set of the PTV; $r(v^i_{OAR}, PTV)$ is a Euclidean distance from the voxel of the OAR to a surface of the PTV The DTH is used to express contours of the PTV obtained through equidistant or different-distance expansion or contraction, and the volume percentage of the overlap of the OAR and each expanded contour of the PTV is calculated. The overlap volume percentages at different distances are used to express the geometric relationship between the PTV and the OAR. In particular, when the distance value is negative, it indicates the invasion of the PTV to the OAR.

In this embodiment, 50 coordinate points (($x_i$, $y_i$) i∈1, 2, ..., 50) are selected from a curve of the DTH equidistantly along an x-axis. The selected 50 discrete coordinate points are used to represent the curve. Each coordinate point includes a volume fraction value $y_i$ (i∈1, 2, ..., 50) and a corresponding distance value $x_i$ (i∈1, 2, ..., 50). $y_i$ denotes the volume fraction value of an $i^{th}$ coordinate. $y_i$ (i∈1, 2, ..., 50) is a vector element used to construct the geometric feature vector of a 50-dimensional DTH. $x_i$ denotes the distance value of the $i^{th}$ coordinate.

Step 3: Subject a geometric feature vector of the DTH in step 2 to dimension reduction through an encoding layer in an autoencoder to obtain a dimension-reduced geometric feature vector of the DTH.

Figure 4:
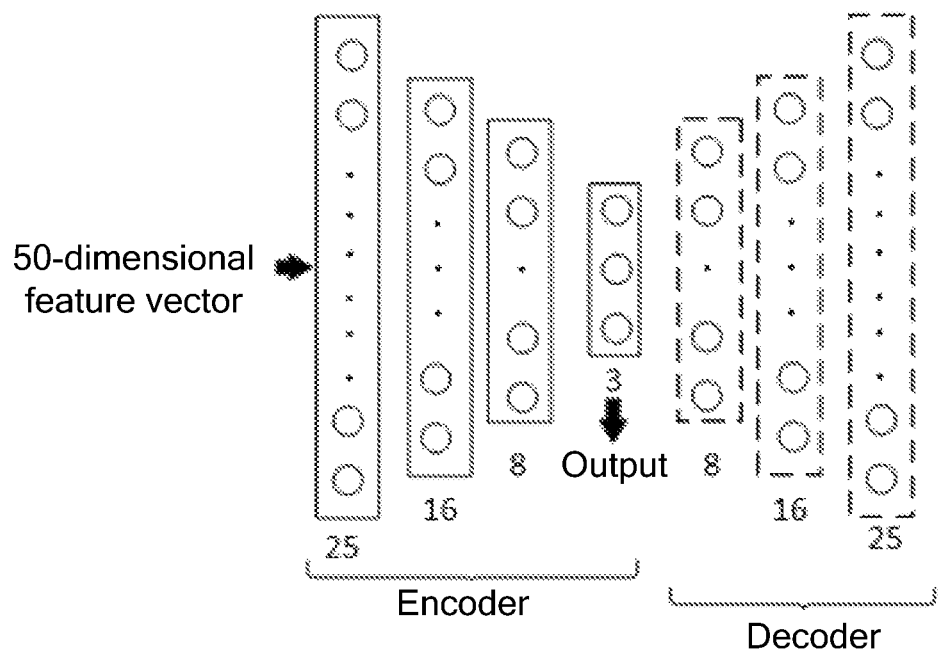
FIG. 4 is a structure diagram of an autoencoder according to Embodiment 1 of the present invention.
Figure 5:
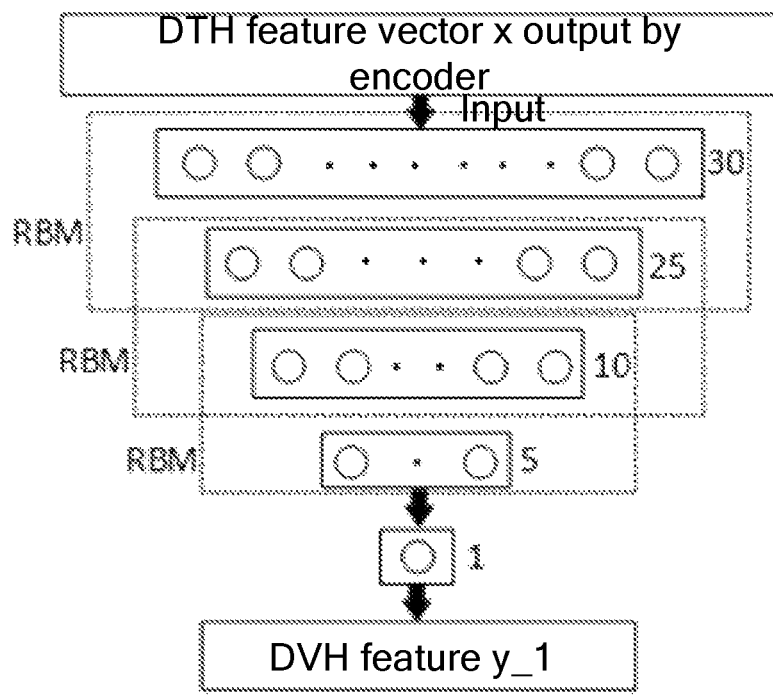
FIG. 5 is a structure diagram of a deep belief network (DBN) according to Embodiment 1 of the present invention.
Figure 6:
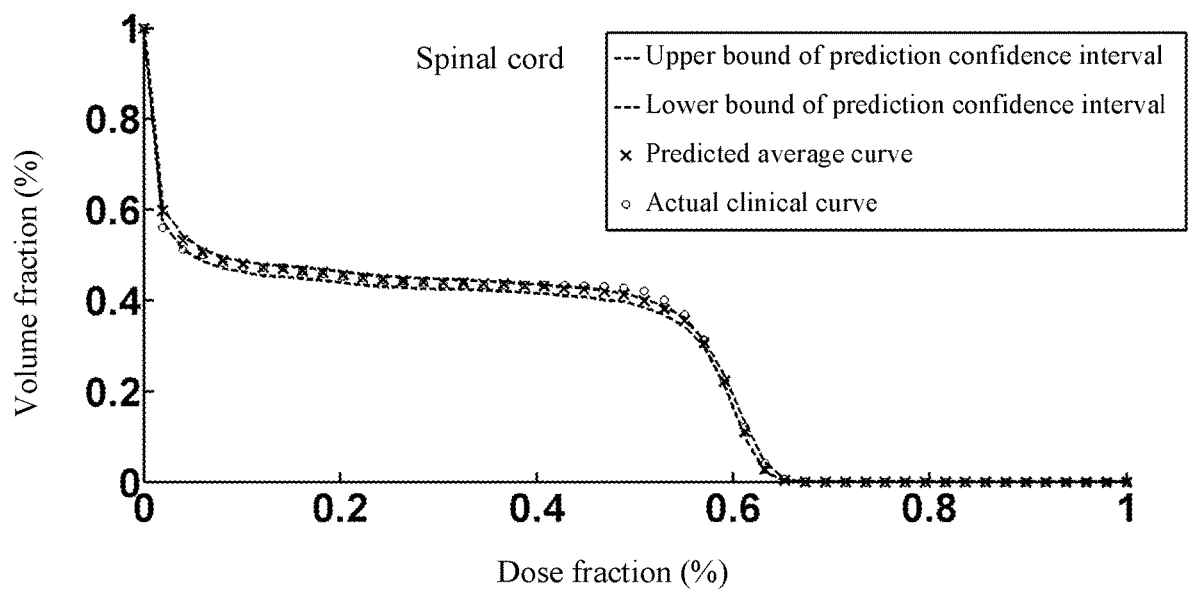
FIG. 6 is a comparison of a model-predicted DVH and an actual clinical DVH of a spinal cord according to Embodiment 2 of the present invention, where, an upper bound indicates a curve with an upper position, and a lower bound indicates a curve with a lower position.
Figure 7:
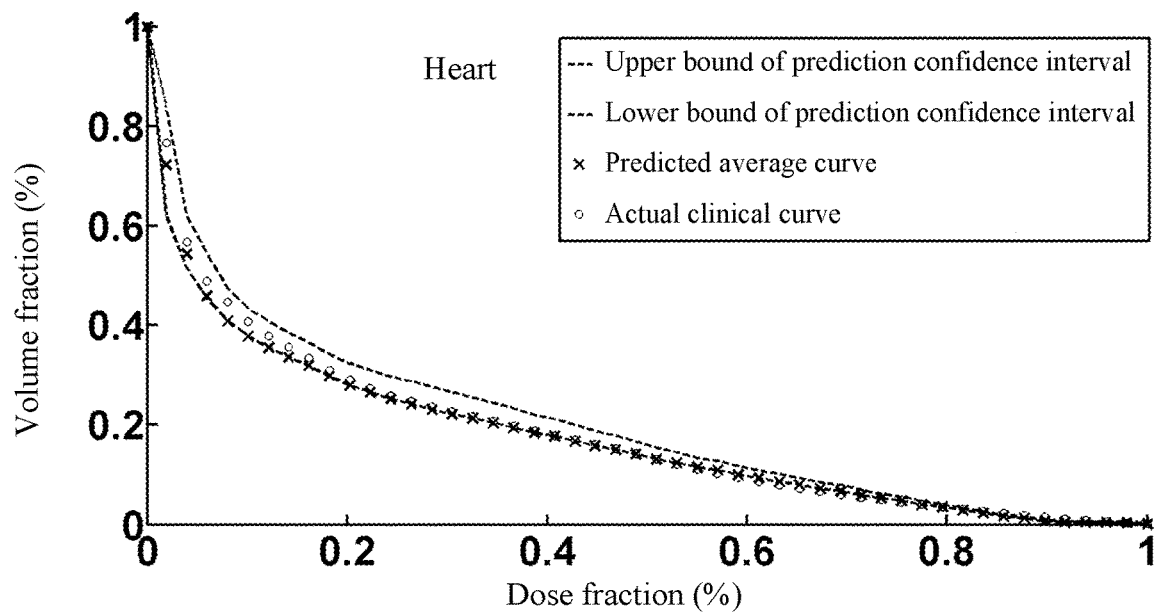
FIG. 7 is a comparison of a model-predicted DVH and an actual clinical DVH of a heart according to Embodiment 2 of the present invention, where, an upper bound indicates a curve with an upper position, and a lower bound indicates a curve with a lower position.
Figure 8:
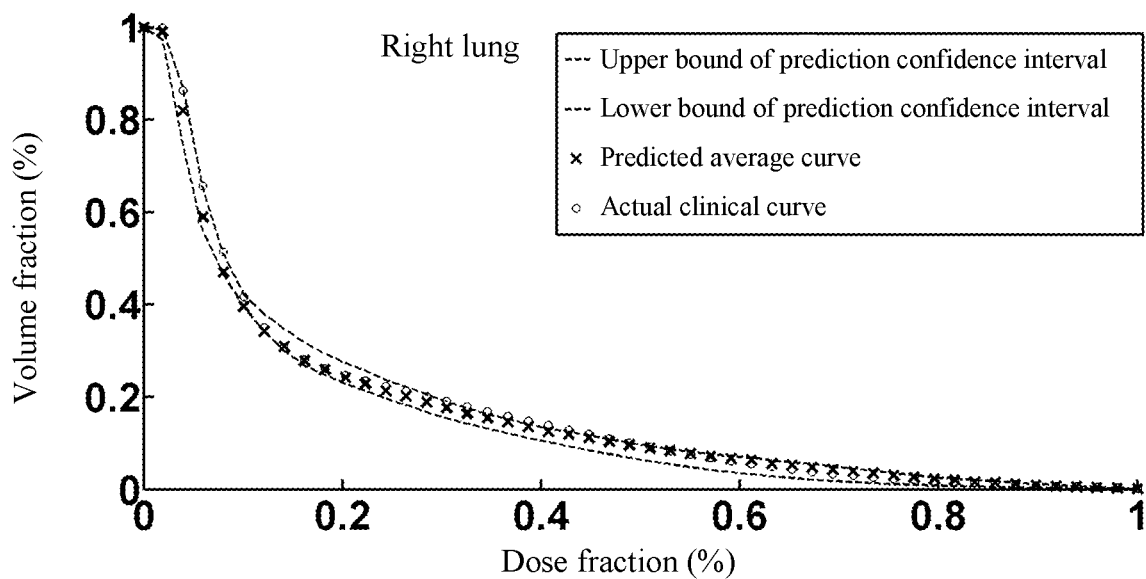
FIG. 8 is a comparison of a model-predicted DVH and an actual clinical DVH of a right lung according to Embodiment 2 of the present invention, where, an upper bound indicates a curve with an upper position, and a lower bound indicates a curve with a lower position.
Figure 9:
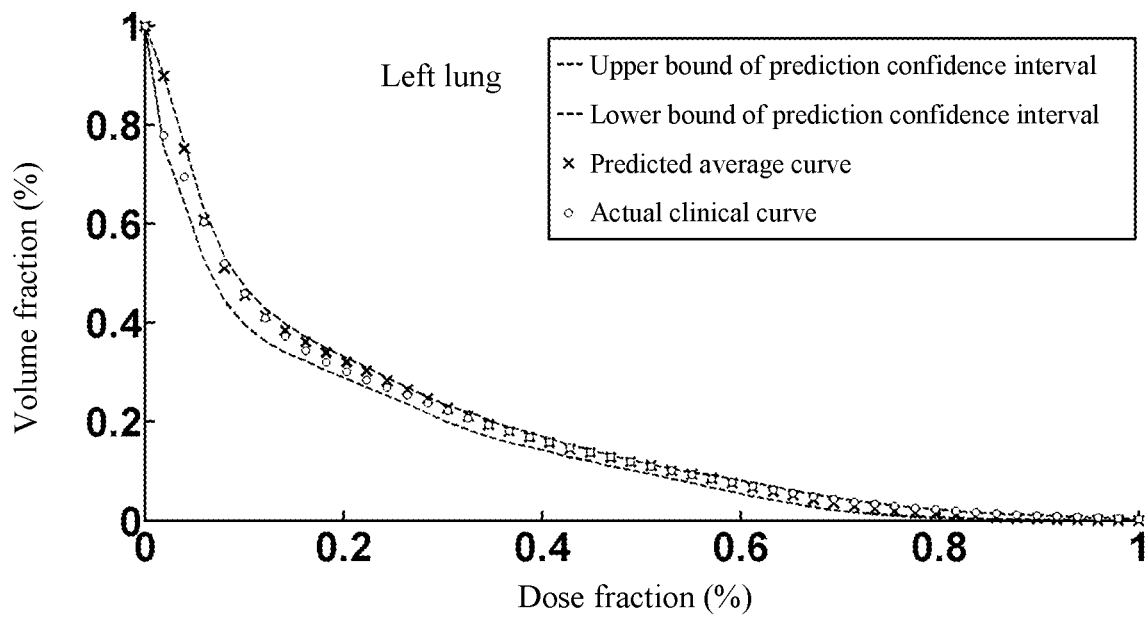
FIG. 9 is a comparison of a model-predicted DVH and an actual clinical DVH of a left lung according to Embodiment 2 of the present invention, where, an upper bound indicates a curve with an upper position, and a lower bound indicates a curve with a lower position.

As shown in FIG. 4, in this embodiment, the autoencoder includes four encoding layers and three decoding layers. The number in the figure refers to the number of neurons in a certain layer of an encoder or a decoder.

Each encoding layer reduces the dimension of an input through the compression of a fully connected layer, and an activation function of each neuron in the encoding layer is:

$$P(h_i = 1 \mid v_i) = \text{sigmoid} \ (c_i + W_i v_i)$$

where, $v_i$ is a feature vector as an input of an $i^{th}$ encoding layer after $(i-1)^{th}$ dimension reduction; $h_i$ is a feature vector as an output of the $i^{th}$ encoding layer after $i^{th}$ dimension reduction; $h_i$, $v_i \in \{0,1\}$; $W_i$ is a weight matrix of the $i^{th}$ encoding layer; $c_i$ is a deviation value of the $i^{th}$ encoding layer, where a dimension of $h_i$ is less than a dimension of Therefore, the encoding layer can reduce the dimension of the input feature vector.

a process of the decoding layer is opposite to a process of the encoding layer. the decoding layer reconstructs an originally input feature vector by increasing a dimension of the input feature vector;

$$P(v_j = 1 \mid h_j) = \text{sigmoid} \ (b_j + W_j h_j)$$

where, $h_j$ is a feature vector as an input of a $j^{th}$ decoding layer after $(j-1)^{th}$ dimension increase; $v_j$ is a feature vector as an output of the $j^{th}$ decoding layer after $i^{th}$ dimension increase; $h_j$, $v_j \in \{0,1\}$; $W_j$ is a weight matrix of the $j^{th}$ decoding layer; $b_j$ is a deviation value of the $j^{th}$ decoding layer, where a dimension of $v_j$ is greater than a dimension of $h_j$. Therefore, the decoding layer can play a role of feature reconstruction.

Step 4: Establish a deep belief network (DBN) model, iterate until convergence, and complete training the DBN model;

VMAT plan data of a patient with esophageal cancer are first acquired as training set data, a CT image and a structural contour image for training are extracted from the training set data, and then a DVH and a DTH for training are calculated.

In this embodiment, the DVH is drawn by using the Matlab-based CERR package, and the built-in function is directly used for extraction. Alternatively, the DVH is drawn by extracting the dose information from a dose chart and the volume information at the corresponding position. The x-axis of the DVH represents the percentage of the dose received by the OAR, and the y-axis represents the volume percentage, indicating that the dose received by the volume is equal to or greater than that indicated on the x-axis.

In this embodiment, 50 coordinate points (($n_j$, $m_j$) j∈1, 2, ..., 50) are selected from a curve of the DVH equidistantly along an x-axis. The selected 50 discrete coordinate points are used to represent the curve. Each coordinate point includes a volume fraction value $m_j$ (j∈1, 2, ..., 50) and a corresponding dose fraction value $n_j$ (j∈1, 2, ..., 50). $m_j$ is a volume fraction value of a $j^{th}$ coordinate. $m_j$ (j∈1, 2, ..., 50) is a vector element used to construct the dose feature vector of a 50-dimensional DVH. $n_j$ is a dose fraction value of the $j^{th}$ coordinate.

For the DTH for training in the training set data, a dimension-reduced three-dimensional (3D) geometric feature vector dt=(dt_1,dt_2,dt_3) of the DTH for training is obtained in Step 3, which is used as an input into the DBN. dt_1, dt_2, dt_3 respectively represent a first dimension component, a second dimension component and a third dimension component of the dimension-reduced 3D geometric feature vector. In Step 3, a dimension-reduced dose feature vector dv=(dv_1,dv_2,dv_3) of the DVH for training is obtained. dv_1, dv_2, dv_3 respectively represent a first dimension component, a second dimension component and a third dimension component of the dimension-reduced 3D dose feature vector.

The DBN model is formed by stacking a plurality of Boltzmann machines. In this embodiment, the DBN model includes three Boltzmann machines. A training process includes pre-training each Boltzmann machine and then stacking the pre-trained Boltzmann machines to be a whole of a DBN for network fine-tuning training.

First, each Boltzmann machine structure is pre-trained, which includes a corresponding visible layer v and hidden layer h.

The Boltzmann machine is iterated during training as follows: map the dimension-reduced geometric feature vector of the DTH in the visible layer to the hidden layer, reconstruct a new geometric feature vector of the DTH through a vector in the hidden layer, and map the reconstructed geometric feature vector of the DTH to the hidden layer, where, this process is expressed as a cycle, and each Boltzmann machine repeats three cycles in the pre-training process to update the weight matrix in the visible layer and the hidden layer of the Boltzmann machine.

An objective loss function in each layer of the DBN is:

$$L(W, dt) = \alpha_s \|g - Y(dt)\|_2^2 + \|dt - Y'(g)\|_2^2 + \alpha_r \|W\|_1$$

where, dt is the dimension-reduced geometric feature vector of the DTH for training, and is further used as an input vector of the visible layer of each Boltzmann machine structure; $\alpha_s \|g-Y(dt)\|_2^2$ is a mean square error from the dimension-reduced geometric feature vector dt of the DTH for training to a feature vector g of the hidden layer; $\alpha_s$ is a constraint coefficient determined empirically in an experiment; a function Y represents a process from the visible layer to the hidden layer in the Boltzmann machine structure, and has an energy function as follows:

$$E(v, h \mid \theta) = -\sum_{i=1}^{n} a_i v_i - \sum_{j=1}^{m} b_j h_j - \sum_{i=1}^{n} \sum_{j=1}^{m} v_i W_{ij} h_j;$$

where, $\theta = \{W_{ij}, a_i, b_j\}$ is a parameter of the Boltzmann machine, which is a real number; $W_{ij}$ is a weight between a visible vector and a hidden vector; the visible layer has a total of i visible vector units (the visible vector refers to the vector dt of the dimension-reduced feature of the DTH for training); $v_i$ is an $i^{th}$ visible vector unit of the visible layer; the hidden layer has a total of j hidden vector units; $h_j$ is a $j^{th}$ hidden vector unit of the hidden layer; $a_i$ is an offset of an $i^{th}$ visible vector unit; $b_j$ is an offset of a $j^{th}$ hidden vector unit; $\|dt-Y'(g)\|_2^2$ is a mean square error between an input provided by the hidden vector g and a new geometric feature vector of the DTH obtained through reconstruction; Y' is an opposite process of Y, and represents the reconstruction of the new geometric feature vector of the DTH by the vector in the hidden layer; $\alpha_r\|W\|_1$ means an ensurement of a sparse expression in an equation by using a non-zero penalty factor; $\|W\|_1$ is L1 regularization of a weight matrix of each layer of the DBN; $\alpha_r$ is a sparse coefficient;

The number of visible vectors i in the visible layer of each Boltzmann machine structure is different. Because the three Boltzmann machine structures are to be stacked in the end, the number j of vector units in the hidden layer of a first layer is equal to the number of vector units in the visible layer of a second layer, that is, the number of outputs from the first layer is equal to the number of inputs into the second layer.

In this embodiment, in a first Boltzmann machine structure, the visible layer has 30 visible vector units, and the hidden layer has 25 hidden vector units. Similarly, in a second Boltzmann machine structure, the visible layer has 25 visible vector units, and the hidden layer has 10 hidden vector units. By analogy, in a third Boltzmann machine structure, the visible layer has 10 visible vector units, and the hidden layer has 5 hidden vector units.

The training process of each Boltzmann machine is subjected to iterative cycles. When the objective loss function is less than 0.05, the objective loss function achieves a stable convergence to complete the training process, a parameter value of the Boltzmann machine is simultaneously stored to obtain a pre-trained Boltzmann machine model, and a plurality of pre-trained Boltzmann machine models are stacked into a pre-trained DBN.

For the pre-trained DBN composed of three Boltzmann machines, the dimension-reduced geometric feature vector of the DTH for training is re-input into the DBN model for fine-tuning training, and the loss function is a mean square error loss function:

$$L(W) = \|dv\_i - D(dt)\|_2^2 \quad i \in [1, 3]$$

When a loss value of the mean square error loss function is less than 0.05, the mean square error loss function achieves a stable convergence, and the parameter value is stored to complete training the DBN model.

A function D denotes a pre-trained DBN model formed by stacking three Boltzmann machine structures. dt is a dimension-reduced geometric feature vector of the DTH for training. dv_i is an $i^{th}$ component of the dimension-reduced dose feature vector of the DVH for training obtained in Step 3. In this embodiment, the dose feature vector of the DVH for training is the feature vector of the 3D DVH, so there are three components. The three components require the establishment of three different DBNs, and the predicted outputs of the three DBNs correspond to a set of dimension-reduced dose feature vectors.

Step 5: Non-linearly fit a correlation between a dose feature vector and the dimension-reduced geometric feature vector by the dimension-reduced geometric feature vector through a trained DBN to obtain a dimension-reduced dose feature vector.

The nonlinear correlation between the dimension-reduced geometric feature vector and the dimension-reduced dose feature vector is fitted by using three DBN models composed of three nonlinear functions. The nonlinear correlation between the dimension-reduced 3D dose feature vector and the dimension-reduced 3D geometric feature vector is:

$$\begin{cases} dv\_1 = F_1(dt\_1, dt\_2, dt\_3) \\ dv\_2 = F_2(dt\_1, dt\_2, dt\_3) \\ dv\_3 = F_3(dt\_1, dt\_2, dt\_3) \end{cases}$$

Fi represents an $i^{th}$ DBN model composed of three Boltzmann machine structures, and the corresponding output is dv_i of the $i^{th}$ dose feature vector. In this embodiment, since the dimension-reduced dose feature is 3D, $i \in [1,3]$. A set of 3D dose feature vectors dvp=(dvp_1,dvp_2,dvp_3) are obtained through the three DBN models.

In the present invention, the dvp is used for verification or clinical processing of the VMAT plan data of a patient with esophageal cancer.

Step 6: Reconstruct the predicted dimension-reduced 3D dose feature vector dvp=(dvp_1,dvp_2,dvp_3) through a decoding layer of the autoencoder structure in Step 3 to obtain a dose feature vector with an original dimension (50-dimensional), and finally obtain a dose-volume histogram (DVH) for predicting an OAR.

Further, preferably, the DVH obtained by the method of the present invention is compared with that obtained by the prior art to further verify the accuracy of the method of the present invention. If the DVH fails to meet a set requirement, the DBN model is further trained.

A 50-dimensional dose feature vector is reconstructed through the decoding layer, and the reconstructed 50-dimensional dose feature vector is used as an ordinate of a coordinate point of a new DVH, that is, $m'_j$ ($j \in 1, 2, \ldots, 50$). A dose fraction value $n_j$ ($j \in 1, 2, \ldots, 50$) is used as an abscissa of the coordinate point. Thus, new 50 coordinate points (($n_j$, $m'_j$), $j \in 1, 2, \ldots, 50$) are obtained. A curve drawn by connecting these 50 coordinate points is the DVH for predicting the OAR by the model.

Embodiment 2

The difference between this embodiment and the above embodiment is that a total of 80 VMAT plans for esophageal cancer were acquired, and they were divided into eight sets evenly, each including 10 plans. In the first set of experiments, a first plan was selected as the test set data, and the rest were used as the training set data. In the second set of experiments, a second plan was selected as the test set data, and the rest were used as the training set data. By analogy, the eight sets of experiments were completed. The average of the eight sets of experiments was used as the final experimental result.

Data Classification and Preprocessing:

The doses corresponding to the patient's OARs were calculated from the acquired high-quality VMAT plans for esophageal cancer. The target OARs in this embodiment were the left lung, the right lung, the heart and the spinal cord. The corresponding DVHs were calculated separately. Each OAR had 80 sets of DVHs. 50 coordinate points in the DVH curve were sampled at equal dose intervals, and each coordinate point was defined by a dose fraction value and a corresponding volume fraction value. The volume fraction value was selected to construct a 50-dimensional DVH feature vector.

According to the acquired high-quality VMAT plans for esophageal cancer, the DTHs of the patient's OARs (left lung, right lung, heart, spinal cord) were calculated separately to describe the geometric relationship between the PTV and the OAR. Each OAR had 80 sets of DTHs. 50 coordinate points with equal distance intervals were selected from the DTH curve. Each coordinate point was defined by a volume fraction value and a corresponding distance value. The volume fraction value was selected to construct a 50-dimensional DTH feature vector.

In the present invention, when the DVH of the OAR of a new patient is predicted, the DTH of the OAR is calculated first, then a 50-dimensional DTH feature vector is established by sampling the DTH curve, and the feature vector is simplified into a 3D feature vector by an autoencoder. The corresponding 3D DVH feature vector can be obtained by mapping the corresponding DBN model. Finally, the DVH feature vector is reconstructed through the decoding layer in the autoencoder, thereby obtaining the predicted DVH of the OAR.

In summary, the present invention is an effective application of the deep learning (DL) technology. Compared with the prediction of the dosimetry features of esophageal cancer radiotherapy by the linear model extracting geometric features and the traditional machine learning (ML) method, the present invention performs automatic assessment of the dose of the OAR of the esophageal radiotherapy plan based on the geometric relationship between OAR and PTV Experiments have shown that the model method can achieve accurate prediction of the DVH and can provide near-optimal parameters for the esophageal treatment plan, which can significantly shorten the time for formulating the esophageal radiotherapy plan and reduce the burden of the radiotherapist.

It should be noted that, in this specification, relationship terms such as "first" and "second" are only used to distinguish an entity or operation from another entity or operation, but do not necessarily require or imply that there is any actual relationship or order between these entities or operations. In addition, terms "include", "comprise", or any other variations thereof are intended to cover non-exclusive inclusions, so that a process, a method, an article, or a device including a series of elements not only includes those elements, but also includes other elements that are not explicitly listed, or also includes inherent elements of the process, the method, the article, or the device. Without more restrictions, the elements defined by the sentence "including a . . . " do not exclude the existence of other identical elements in the process, method, article, or device including the elements.

The above embodiments are only used to explain the technical solutions of the disclosure, and are not intended to limit the same. Although the disclosure is described in detail with reference to the above embodiments, those of ordinary skill in the art should understand that they can still modify the technical solutions described in the above embodiments, or make equivalent substitutions on some technical features therein. These modifications or substitutions do not make the essence of the corresponding technical solutions deviate from the spirit and scope of the technical solutions of the embodiments of the disclosure.

What is claimed is:

1. A deep learning dosimetry assessment method for an organ at risk (OAR) in an esophageal radiotherapy plan, comprising:
    step 1: acquiring, by at least one processor, volumetric-modulated arc therapy (VMAT) plan data of a patient with esophageal cancer, comprising a computed tomography (CT) image and a structural contour image that are extracted;
    step 2: calculating, by the at least one processor, the VMAT plan data for the esophageal cancer to obtain a distance-target histogram (DTH);
    step 3: subjecting, by the at least one processor, a geometric feature vector of the DTH in step 2 to dimension reduction through an encoding layer in an autoencoder structure to obtain a dimension-reduced geometric feature vector;
    step 4: establishing, by the at least one processor, a deep belief network (DBN) model, iterating until convergence, and completing training the DBN model;
    step 5: non-linearly fitting, by the at least one processor, a correlation between a dose feature vector and the dimension-reduced geometric feature vector by the dimension-reduced geometric feature vector through a trained DBN to obtain a dose feature vector with a dimension being identical to a dimension of the dimension-reduced geometric feature vector;
    step 6: reconstructing, by the at least one processor, the dose feature vector of step 5 through a decoding layer of the autoencoder structure to obtain a dose feature vector with a dimension being identical to a dimension of the geometric feature vector before the dimension reduction, and obtaining a dose-volume histogram (DVH) based on the reconstructed dose feature vector; and
    step 7: formulating, by the at least one processor, the esophageal radiotherapy plan based on the DVH, and performing an esophageal radiotherapy procedure on the patient based on the esophageal radiotherapy plan.

2. The deep learning dosimetry assessment method for the OAR in the esophageal radiotherapy plan according to claim 1, wherein in step 2, the DTH is established by calculating a volume percentage of the OAR:

$$r(v_{OAR}^j, PTV) = \min_k \{\|v_{OAR}^j - v_{PTV}^k\| \mid v_{PTV}^k \in S_{PTV}\}$$

wherein, $v_{OAR}^i$ is an $i^{th}$ voxel of the OAR; $v_{PTV}^K$ is a $k^{th}$ voxel of a planning target volume (PTV); $S_{PTV}$ is a voxel set of the PTV; $r(v_{OAR}^i, PTV)$ is a Euclidean distance from the voxel of the OAR to a surface of the PTV.

3. The deep learning dosimetry assessment method for the OAR in the esophageal radiotherapy plan according to claim 2, wherein n coordinate points $((x_i, y_i), i \in 1, 2, \ldots, n)$ are selected from a curve of the DTH equidistantly along an x-axis; the selected n discrete coordinate points are used to represent the curve; each coordinate point comprises a volume fraction value $y_i$ ($i \in 1, 2, \ldots, n$) and a corresponding distance value $x_i$ ($i \in 1, 2, \ldots, n$); $y_i$ denotes the volume fraction value of an $i^{th}$ coordinate; $y_i$ ($i \in 1, 2, \ldots, n$) is a vector element used to construct a geometric feature vector of an n-dimensional DTH; $x_i$ denotes the distance value of the $i^{th}$ coordinate.

4. The deep learning dosimetry assessment method for the OAR in the esophageal radiotherapy plan according to claim 1, wherein an encoder is composed of a plurality of encoding layers and a plurality of decoding layers;

each encoding layer reduces a dimension of an input through a compression of a fully connected layer, and an activation function of each neuron in the encoding layer is:

$$P(h_i = 1 \mid v_i) = \text{sigmoid }(c_i + W_i v_i)$$

wherein, $v_i$ is a feature vector as an input of an $i^{th}$ encoding layer after $(i-1)^{th}$ dimension reduction; $h_i$ is a feature vector as an output of the $i^{th}$ encoding layer after $i^{th}$ dimension reduction; $h_i, v_i \in \{0,1\}$; $W_i$ is a weight matrix of the $i^{th}$ encoding layer; $c_i$ is a deviation value of the $i^{th}$ encoding layer, wherein a dimension of $h_i$ is less than a dimension of $v_i$;

a process of the decoding layer is opposite to a process of the encoding layer; the decoding layer reconstructs an originally input feature vector by increasing a dimension of the input feature vector;

$$P(v_j = 1 \mid h_j) = \text{sigmoid}(b_j + W_j h_j)$$

wherein, $h_j$ is a feature vector as an input of a $j^{th}$ decoding layer after $(j-1)^{th}$ dimension increase; $v_j$ is a feature vector as an output of the $j^{th}$ decoding layer after $j^{th}$ dimension increase; $h_j, v_j \in \{0,1\}$; $W_j$ is a weight matrix of the $j^{th}$ decoding layer; $b_j$ is a deviation value of the $j^{th}$ decoding layer, wherein a dimension of $v_j$ is greater than a dimension of $h_j$.

5. The deep learning dosimetry assessment method for the OAR in the esophageal radiotherapy plan according to claim 1, wherein in step 4, the DBN model is formed by stacking a plurality of Boltzmann machines; a training process comprises pre-training each of the Boltzmann machines and then stacking pre-trained Boltzmann machines to be a whole of a DBN for network fine-tuning training.

6. The deep learning dosimetry assessment method for the OAR in the esophageal radiotherapy plan according to claim 5, wherein the VMAT plan data of the patient with the esophageal cancer for training are acquired as training set data, the CT image for training and the structural contour image for training are extracted from the training set data, and the DVH for training and the DTH for training are calculated; the dose feature vector of the DVH for training and the geometric feature vector of the DTH for training are calculated; a dimension-reduced dose feature vector of the DVH for training and a dimension-reduced geometric feature vector of the DTH for training are obtained through the decoding layer of the autoencoder structure;

each Boltzmann machine structure is pre-trained, wherein the each Boltzmann machine structure comprises a corresponding visible layer v and hidden layer h;

iterating steps of the Boltzmann machine in the training process comprise: mapping the dimension-reduced geometric feature vector of the DTH in the visible layer to the hidden layer, reconstructing a new geometric feature vector of the DTH through a vector in the hidden layer, and mapping a reconstructed geometric feature vector of the DTH to the hidden layer, wherein, this process is expressed as a cycle, and each Boltzmann machine repeats three cycles in a pre-training process to update weight matrices in the visible layer and the hidden layer of the Boltzmann machine;

wherein, an objective loss function in each layer of the DBN is:

$$L(W, dt) = \alpha_s \|g - Y(dt)\|_2^2 + \|dt - Y'(g)\|_2^2 + \alpha_r \|W\|_1$$

wherein, dt is the dimension-reduced geometric feature vector of the DTH for training, and is further used as an input vector of the visible layer of each Boltzmann machine structure; $\alpha_s \|g-Y(dt)\|_2^2$ is a mean square error from the dimension-reduced geometric feature vector dt of the DTH for training to a feature vector g of the hidden layer; $\alpha_s$ is a constraint coefficient determined empirically in an experiment; a function Y(dt) represents a process from the visible layer to the hidden layer in the Boltzmann machine structure, and has an energy function as follows:

$$E(v, h \mid \theta) = -\sum_{i=1}^{n} a_i v_i - \sum_{j=1}^{m} b_j h_j - \sum_{i=1}^{n} \sum_{j=1}^{m} v_j W_{ij} h_j$$

wherein, $\theta = \{W_{ij}, a_i, b_j\}$ is a parameter of the Boltzmann machine; $W_{ij}$ is a weight between a visible vector and a hidden vector; the visible layer has a total of i visible vector units; the hidden layer has a total of j hidden vector units; $a_i$ is an offset of an $i^{th}$ visible vector unit; $b_j$ is an offset of a $j^{th}$ hidden vector unit; $\|dt-Y'(g)\|_2^2$ is a mean square error between an input provided by the hidden vector g and a new geometric feature vector of the DTH obtained through reconstruction; Y' (g) is an opposite process of Y, and represents the reconstruction of the new geometric feature vector of the DTH by the vector in the hidden layer; $\alpha_r \|W\|_1$ means an ensurement of a sparse expression in an equation by using a non-zero penalty factor; $\|W\|1$ is L1 regularization of a weight matrix of each layer of the DBN; $\alpha_r$ is a sparse coefficient;

the training process of each Boltzmann machine is subjected to iterative cycles; when the objective loss function is less than a set threshold, the objective loss function achieves a stable convergence to complete the training process, a parameter value of the Boltzmann machine is simultaneously stored to obtain a pre-trained Boltzmann machine model, and a plurality of pre-trained Boltzmann machine models are stacked into a pre-trained DBN.

7. The deep learning dosimetry assessment method for the OAR in the esophageal radiotherapy plan according to claim 6, wherein the dimension-reduced geometric feature vector of the DTH for training is re-input into the pre-trained DBN model for the fine-tuning training, and the loss function is a mean square error loss function:

$$L(W) = \frac{1}{2} \|dv\_i - D(dt)\|_2^2$$

when a loss value of the mean square error loss function is less than the set threshold, the mean square error loss function achieves a stable convergence, and the parameter value is stored to complete training the DBN model;

wherein, a function D(dt) denotes a pre-trained DBN model formed by stacking three Boltzmann machine structures; dt is the dimension-reduced geometric feature vector of the DTH for training; dv_i is an $i^{th}$ component of the dimension-reduced dose feature vector of the DVH for training obtained in step 3; i components require i different DBNs, and predicted outputs of the i DBNs correspond to a set of dimension-reduced dose feature vectors.

8. The deep learning dosimetry assessment method for the OAR in the esophageal radiotherapy plan according to claim 1, wherein in step 6, an n-dimensional dose feature vector is reconstructed through the decoding layer, and the reconstructed n-dimensional dose feature vector is used as an ordinate of a coordinate point of a new DVH, that is, $m'_j$ ($j \in 1, 2, \ldots, n$); a dose fraction value $n_j$ ($j \in 1, 2, \ldots, n$) is used as an abscissa of the coordinate point; wherein, new n coordinate points (($n_j$, $m'_j$), $j \in 1, 2, \ldots, n$) are obtained; a curve drawn by connecting the n coordinate points is the DVH.

9. A deep learning dosimetry assessment system for an organ at risk (OAR) in an esophageal radiotherapy plan, comprising:
at least one processor;
an encoding layer, configured to subject a geometric feature vector of a distance-target histogram (DTH) to dimension reduction to obtain a dimension-reduced geometric feature vector;
a deep belief network (DBN) model, wherein a correlation between a dose feature vector and the dimension-reduced geometric feature vector is non-linearly fitted by the dimension-reduced geometric feature vector through a trained DBN to obtain a dose feature vector with a dimension being identical to a dimension of the dimension-reduced geometric feature vector;
a decoding layer, configured to reconstruct the dose feature vector to obtain a dose feature vector with a dimension being identical to a dimension of the geometric feature vector before the dimension reduction;
wherein the at least one processor is configured to perform the following steps:

step 1: acquiring volumetric-modulated arc therapy (VMAT) plan data of a patient with esophageal cancer, comprising a computed tomography (CT) image and a structural contour image that are extracted;
step 2: calculating the VMAT plan data for the esophageal cancer to obtain the DTH;
step 3: subjecting the geometric feature vector of the DTH in step 2 to dimension reduction through the encoding layer in an autoencoder structure to obtain the dimension-reduced geometric feature vector;
step 4: establishing the deep belief network (DBN) model, iterating until convergence, and completing training the DBN model;
step 5: non-linearly fitting the correlation between the dose feature vector and the dimension-reduced geometric feature vector by the dimension-reduced geometric feature vector through the trained DBN to obtain the dose feature vector with the dimension being identical to a dimension of the dimension-reduced geometric feature vector;
step 6: reconstructing the dose feature vector of step 5 through the decoding layer of the autoencoder structure to obtain the dose feature vector with the dimension being identical to the dimension of the geometric feature vector before the dimension reduction, and obtaining a dose-volume histogram (DVH) based on the reconstructed dose feature vector; and
step 7: formulating the esophageal radiotherapy plan based on the DVH, and performing an esophageal radiotherapy based on the patient based on the esophageal radiotherapy plan.

10. The deep learning dosimetry assessment system for the OAR in the esophageal radiotherapy plan according to claim 9, wherein the DBN model is formed by stacking a plurality of Boltzmann machines; a training process comprises pre-training each of the Boltzmann machines and then stacking pre-trained Boltzmann machines to be a whole of a DBN for network fine-tuning training.

* * * * *